(12) United States Patent
McDowell

(10) Patent No.: US 11,844,894 B2
(45) Date of Patent: *Dec. 19, 2023

(54) Y-CONNECTOR FOR BLOOD PROCESSING SYSTEM AND DISPOSABLE SET CONTAINING SAME

(71) Applicant: Haemonetics Corporation, Boston, MA (US)

(72) Inventor: Christopher S. McDowell, Murray, UT (US)

(73) Assignee: Haemonetics Corporation, Boston, MA (US)

( * ) Notice: Subject to any disclaimer, the term of this patent is extended or adjusted under 35 U.S.C. 154(b) by 93 days.

This patent is subject to a terminal disclaimer.

(21) Appl. No.: 17/322,015

(22) Filed: May 17, 2021

(65) Prior Publication Data

US 2021/0268164 A1 Sep. 2, 2021

Related U.S. Application Data

(63) Continuation of application No. 16/308,848, filed as application No. PCT/US2017/037459 on Jun. 14, 2017, now Pat. No. 11,135,349.

(Continued)

(51) Int. Cl.
*A61M 1/36* (2006.01)
*A61M 1/34* (2006.01)
(Continued)

(52) U.S. Cl.
CPC .......... *A61M 1/367* (2013.01); *A61M 1/3496* (2013.01); *A61M 39/04* (2013.01);
(Continued)

(58) Field of Classification Search
CPC ........ G01N 1/10; A61M 1/367; A61M 1/3496
See application file for complete search history.

(56) References Cited

U.S. PATENT DOCUMENTS

| | | | |
|---|---|---|---|
| 4,707,335 A | 11/1987 | Fentress et al. | |
| 4,988,342 A | 1/1991 | Herweck et al. | |

(Continued)

FOREIGN PATENT DOCUMENTS

| | | |
|---|---|---|
| CN | 2845811 Y | 12/2006 |
| CN | 201073458 Y | 6/2008 |

(Continued)

OTHER PUBLICATIONS

International Search Report and Written Opinion for Application No. PCT/US2017/037459, dated Sep. 7, 2017, 13 pages.

(Continued)

*Primary Examiner* — Paul M. West
(74) *Attorney, Agent, or Firm* — McCarter & English, LLP; Jonathan C. Lovely

(57) ABSTRACT

A tubing set for a blood processing system includes a first connector, a first tube, and a second tube. The first connector is configured to connect to a separation device within the blood processing system, and has a first inlet configured to be fluidly connected to an outlet of the separation device. The first connector also has an outlet and a second inlet. The first tube fluidly connects to the outlet and fluidly connects the separation device and a blood component storage container. The second tube is fluidly connected to the second inlet and fluidly connects the separation device and a saline storage container. The second tube may include a second connector that connects to the saline storage container.

36 Claims, 14 Drawing Sheets

Related U.S. Application Data

(60) Provisional application No. 62/350,930, filed on Jun. 16, 2016.

(51) Int. Cl.

| | | |
|---|---|---|
| *G01N 1/10* | (2006.01) | |
| *A61M 39/04* | (2006.01) | |
| *A61M 39/08* | (2006.01) | |
| *A61M 39/20* | (2006.01) | |
| *G01N 33/48* | (2006.01) | |
| *A61M 39/02* | (2006.01) | |

(52) U.S. Cl.
CPC ............ *A61M 39/08* (2013.01); *A61M 39/20* (2013.01); *G01N 1/10* (2013.01); *G01N 33/48* (2013.01); *A61M 2039/0202* (2013.01); *A61M 2202/0415* (2013.01); *A61M 2205/583* (2013.01)

(56) References Cited

U.S. PATENT DOCUMENTS

| | | | |
|---|---|---|---|
| 5,112,298 A | 5/1992 | Prince et al. | |
| 5,160,615 A | 11/1992 | Takagi et al. | |
| 5,382,242 A | 1/1995 | Horton et al. | |
| 5,527,472 A | 6/1996 | Bellotti et al. | |
| 5,780,222 A | 7/1998 | Peddada et al. | |
| 5,951,519 A | 9/1999 | Utterberg | |
| 5,954,971 A | 9/1999 | Pages et al. | |
| 5,971,948 A | 10/1999 | Pages et al. | |
| 6,220,453 B1 | 4/2001 | Kitajima et al. | |
| 6,312,950 B1 | 11/2001 | Ohmura et al. | |
| 6,328,726 B1 | 12/2001 | Ishida et al. | |
| 6,358,420 B2 | 3/2002 | Blickhan et al. | |
| 6,855,119 B2 | 2/2005 | Rivera et al. | |
| 11,135,349 B2 * | 10/2021 | McDowell | G01N 33/48 |
| 2001/0052497 A1 | 12/2001 | Blickhan et al. | |
| 2002/0177799 A1 | 11/2002 | Rivera et al. | |
| 2004/0238444 A1 | 12/2004 | Ragusa | |
| 2012/0136341 A1 | 5/2012 | Appling et al. | |
| 2019/0307941 A1 | 10/2019 | McDowell | |

FOREIGN PATENT DOCUMENTS

| | | |
|---|---|---|
| CN | 203139214 U | 8/2013 |
| EP | 0987034 A2 | 3/2000 |
| JP | 3-297471 A | 12/1991 |
| JP | 9-501340 A | 2/1997 |
| JP | 11-197236 A | 7/1999 |
| JP | 11-295298 A | 10/1999 |
| JP | 2000-83649 A | 3/2000 |
| RU | 2285543 C2 | 10/2006 |

OTHER PUBLICATIONS

Russian Decision to Grant for Application No. 2019100696, dated Nov. 24, 2020, 7 pages.

* cited by examiner

Y-CONNECTOR FOR BLOOD PROCESSING SYSTEM AND DISPOSABLE SET CONTAINING SAME

PRIORITY

This application is a continuation of and claims priority from co-pending U.S. application Ser. No. 16/308,848, entitled "Y-Connector for Blood Processing System and Disposable Set Containing Same," filed Dec. 11, 2018, and naming Christopher McDowell as inventor, the disclosure of which is incorporated herein, in its entirety, by reference.

U.S. application Ser. No. 16/308,848 is a 35 U.S.C. § 371 national stage filing of International Application No. PCT/US2017/037459, entitled "Y-Connector for Blood Processing System and Disposable Set Containing Same," filed on Jun. 14, 2017, and naming Christopher McDowell as inventor, the disclosure of which is incorporated herein, in its entirety, by reference.

International Application No. PCT/US2017/037459 claims priority from U.S. Provisional Patent Application No. 62/350,930, filed Jun. 16, 2016, entitled "Y-Connector for Blood Processing System and Disposable Set Containing Same," and naming Christopher McDowell as inventor, the disclosure of which is incorporated herein, in its entirety by reference.

TECHNICAL FIELD

The present invention relates to systems and methods for blood apheresis, and more particularly to disposable sets and connectors for blood processing systems.

BACKGROUND ART

Apheresis is a procedure in which individual blood components can be separated and collected from whole blood temporarily withdrawn from a subject. Typically, whole blood is withdrawn through a needle inserted into a vein of the subjects arm and into a cell separator, such as a centrifugal bowl. Once the whole blood is separated into its various components, one or more of the components can be removed from the centrifugal bowl. The remaining components can be returned to the subject along with optional compensation fluid to make up for the volume of the removed component. The process of drawing and returning continues until the quantity of the desired component has been collected, at which point the process is stopped. A central feature of apheresis systems is that the processed but unwanted components are returned to the donor. Separated blood components may include, for example, a high density component such as red blood cells, an intermediate density component such as platelets or white blood cells, and a lower density component such as plasma.

Set up of the blood processing system and installation of the tubing and disposable components required for processing may be complex. Additionally, if the tubing is not installed properly, the tubing may become kinked/twisted and/or may be connected to the wrong components. This not only negatively impacts the performance of the system (e.g., if the tubing is kinked/twisted), it also puts the donor/patient at risk (e.g., if the tubing is connected to the wrong components).

SUMMARY OF THE INVENTION

In accordance with some embodiments of the present invention, a tubing set for a blood processing system includes a first connector that may be connected to a separation device within the blood processing system. The first connector may have a first inlet, a second inlet, and an outlet. The first inlet may be fluidly connected to an outlet of the separation device. A first tube, which is fluidly connected to the outlet of the connector, may fluidly connect the separation device and a blood component storage container. A second tube, which is fluidly connected to the second inlet of the connector, may fluidly connect the separation device and a saline storage container. The second tube may include a second connector (e.g., a spike) that is configured to connect to the saline storage container.

The tubing set may also include a cap that covers the inlet of the first connector when the first connector is not connected to the separation device. The cap may be tethered to the first connector. The cap may make a liquid-tight seal on the first connector. For example, the cap may include a rib extending from an inner surface of the cap, and the rib may seal against an outer surface of the first connector. Additionally or alternatively, the cap may include a tab that extends from a surface of the body of the cap. The tab may allow a user to remove the cap from the first connector when connected.

In some embodiments, the second tube may be tinted and/or include one or more markings, or the first and second tubes may be color coded. The marking(s) may indicate that the second tube is configured to be connected to the saline storage container and may, for example, include text indicating that the second tube is to be connected to the saline storage container. Additionally or alternatively, the first tube may include marking(s) to indicate that the first tube is to be connected to the blood component storage container. The marking(s) may include dots and/or lines.

The first tube may have a first portion and second portion. The second portion may include a pre-curved section, and one end of the pre-curved section may connect to the blood component storage container. The pre-curved section may be integrally formed with the second portion or may be solvent bonded to the second portion. The first tube may also include a sample site located between the first portion and the second portion. The sample site may include a sample site inlet fluidly connected to the first portion, a sample site outlet fluidly connected to the second portion, and a sample port. The sample port may include a septum that seals the sample port. The sample site may receive a sample collection container holder, for example, during sampling of the collected blood component.

In further embodiments, the outlet may include a first fluid path fluidly connecting the first inlet and the outlet, and the second inlet may include a second fluid path fluidly connecting the inlet and the second inlet. The diameter of the first and second fluid paths may expand/increase toward the outlet and second inlet. The blood component storage container may be a plasma container.

In accordance with additional embodiments, a connector for a blood processing system includes a connector body defining the structure of the connector, a first port, a second port, and a third port. The first port may connect directly to an outlet of a separation device of the blood processing system. The second port may be fluidly connected to the first port and to a first tube that, in turn, fluidly connects the second port and a blood component storage container. The third port may be fluidly connected to the first port and to a second tube that, in turn, fluidly connects the third port and a saline storage container.

The connector may also include a cap that covers the first port when the first port is not connected to the separation device. The cap may be tethered to the connector body. The cap may create a liquid-tight seal on the first connector. For example, the cap may have a rib that extends from an inner surface of the cap. The rib may seal against an outer surface of the first connector. Additionally or alternatively, the cap may include a tab that extends from a surface of the body of the cap. The tab may allow a user to remove the cap from the first connector when connected.

In some embodiments, the connector may include a first flow channel that extends, at least partially, through the connector body and fluidly connects the first port and the second port. Additionally or alternatively, the connector may also have a second flow channel that extends, at least partially, through the connector body and fluidly connects the first port and the third port. The diameter of the first flow channel and/or the second flow channel may expand toward the second port and the third port. The blood component storage container may be a plasma container.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Illustrative embodiments of the present invention provide a disposable set for a blood processing system. The disposable set includes a connector (e.g., a y-connector/3-port connector) with an inlet that connects to the outlet of a separation device within the blood processing system. The set also includes a first tube that fluidly connects the outlet of the connector and a blood component storage container, and a second tube that fluidly connects a second inlet of the connector to a saline storage container. The connector and disposable set help prevent the tubing from kinking and twisting, and ease the installation procedure. Details of the illustrative embodiments are discussed below.

Figure 1:
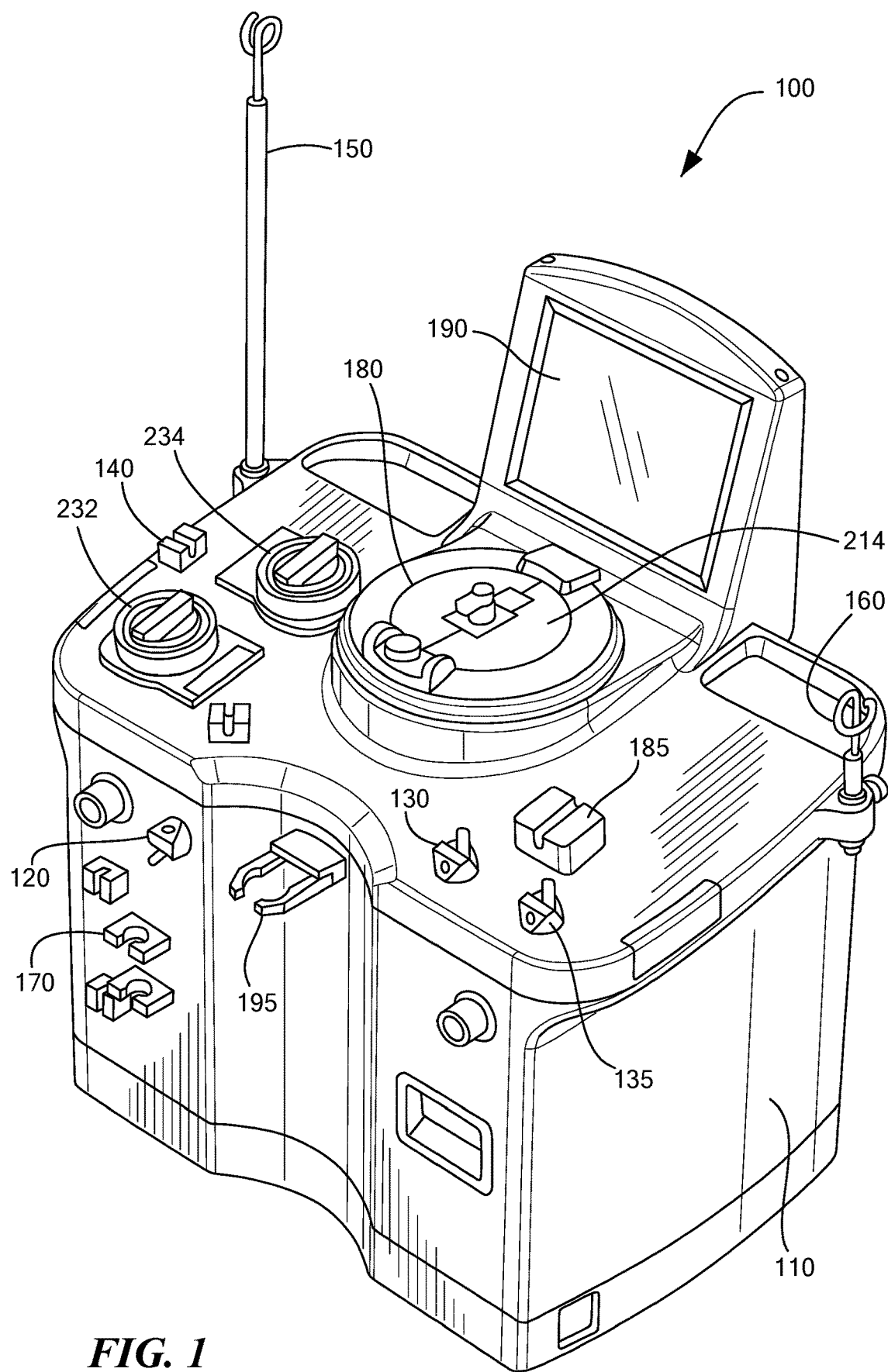
FIG. 1 schematically shows a perspective view of a blood processing system in accordance with some embodiments of the present invention.
Figure 2:
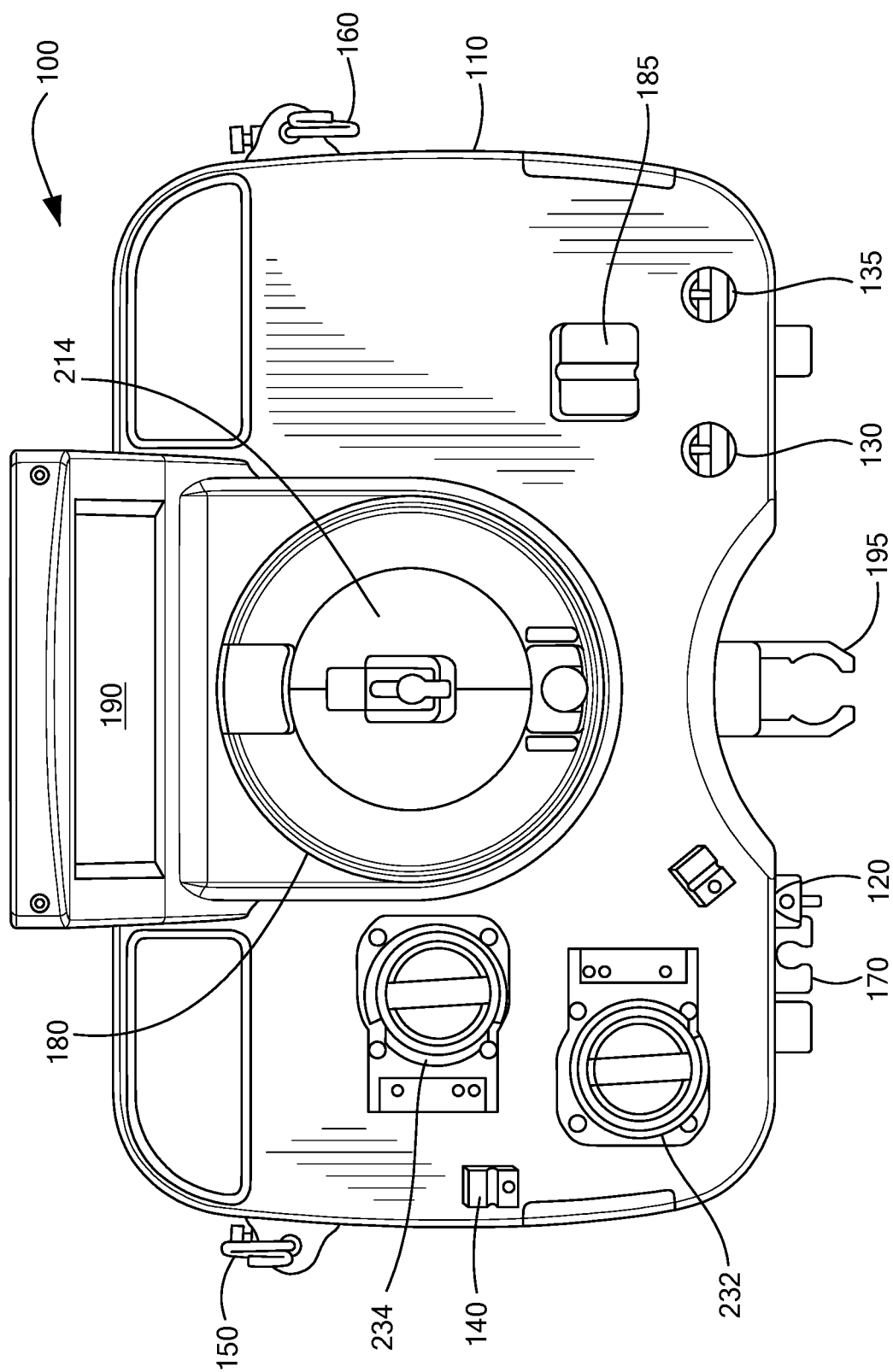
FIG. 2 schematically shows a top view of the blood processing system of FIG. 1, in accordance with some embodiments of the present invention.
Figure 3:
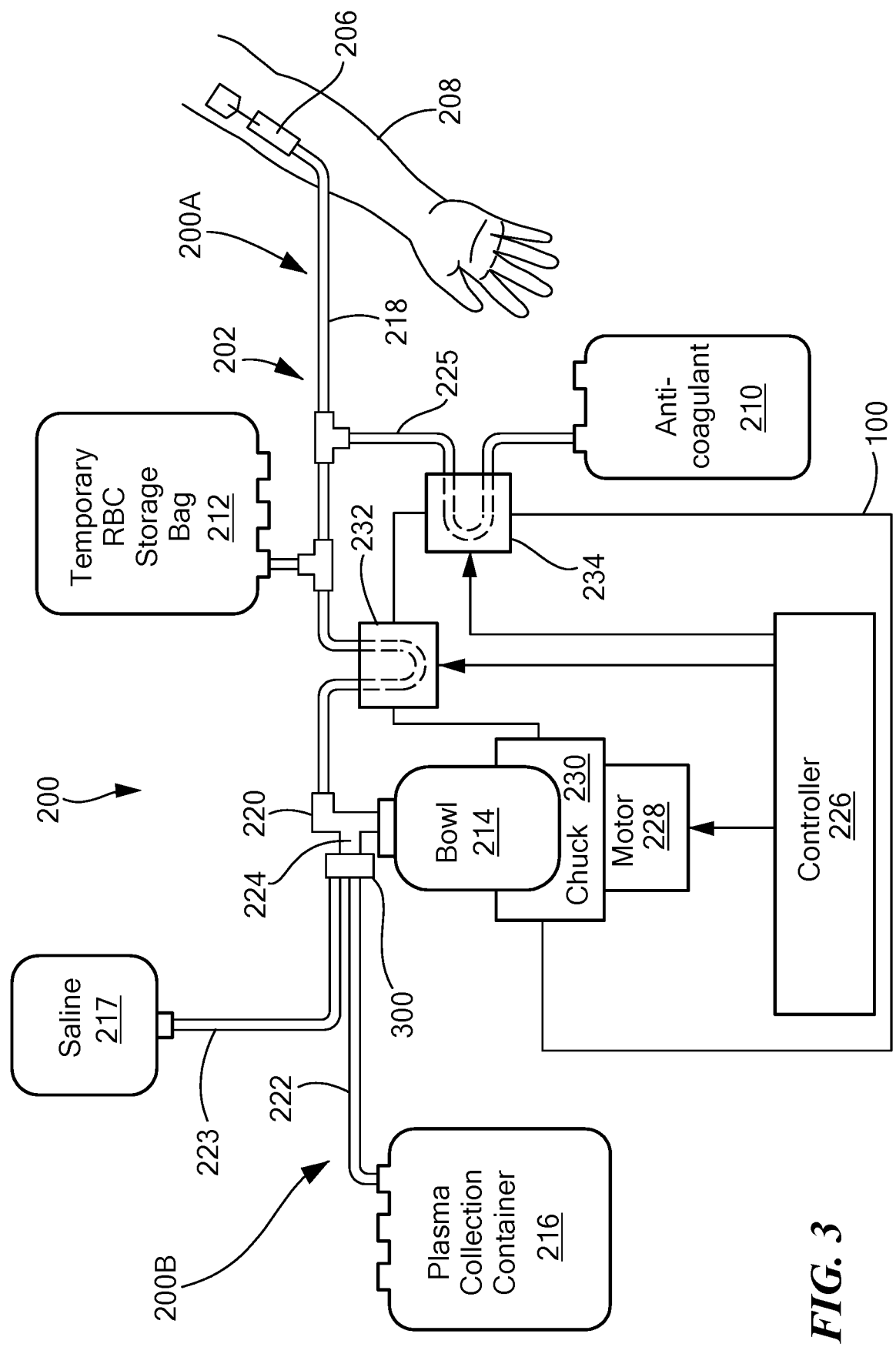
FIG. 3 schematically shows a disposable set installed within the blood processing system of FIG. 1, in accordance with some embodiments of the present invention.

As shown in FIGS. 1 and 2, the blood processing system 100 includes a cabinet 110 that houses the main components of the system 100 (e.g., the non-disposable components). Within the cabinet 110, the system 100 may include a first/blood pump 232 that draws whole blood from a subject, and a second/anticoagulant pump 234 that pumps anticoagulant through the system 100 and into the drawn whole blood. Additionally, the system 100 may include a number of valves that may be opened and/or closed to control the fluid flow through the system 100. For example, the system 100 may include a donor valve 120 that may open and close to selectively prevent and allow fluid flow through a donor line 218 (e.g., an inlet line; FIG. 3), and a plasma valve 130 that selectively prevents and allows fluid flow through an outlet/plasma line 222 (FIG. 3). Some embodiments may also include a saline valve 135 that selectively prevents and allows saline to flow through a saline line 223.

To facilitate the connection and installation of a disposable set and to support the corresponding fluid containers, the system 100 may include an anticoagulant pole 150 on which the anticoagulant solution container 210 (FIG. 3) may be hung, and a saline pole 160 on which a saline solution container 217 (FIG. 3) may be hung (e.g., if the procedure being performed requires the use of saline). Additionally, in some applications, it may be necessary and/or desirable to filter the whole blood drawn from the subject for processing. To that end, the system 100 may include blood filter holder 170 in which the blood filter (located on the disposable set) may be placed.

As discussed in greater detail below, apheresis systems 100 in accordance with embodiments of the present invention withdraw whole blood from a subject through a venous access device 206 (FIG. 3) using the blood pump 232. As the system 100 withdraws the whole blood from the subject, the whole blood enters a blood component separation device 214, such as a Latham type centrifuge (or other type of separation chamber/device, such as, without limitation, an integral blow-molded centrifuge bowl, as described in U.S. Pat. Nos. 4,983,158 and 4,943,273, which are hereby incorporated by reference). The blood component separation device 214 separates the whole blood into its constituent components (e.g., red blood cells, white blood cell, plasma, and platelets). Accordingly, to facilitate operation of the separation device 214, the system 100 may also include a well 180 in which the separation device 214 may be placed and in which the separation device 214 rotates (e.g., to generate the centrifugal forces required to separate the whole blood).

To allow the user/technician to monitor the system operation and control/set the various parameters of the procedure, the system 100 may include a user interface 190 (e.g., a touch screen device) that displays the operation parameters, any alarm messages, and buttons which the user/technician may depress to control the various parameters. Additional components of the blood processing system 100 are discussed in greater detail below (e.g., in relation to the system operation).

Fla 3 is a schematic block diagram of the blood processing system 100 and a disposable collection set 200 (with an inlet disposable set 200A and an outlet disposable set 200B) that may be loaded onto/into the blood processing system 100, in accordance with various embodiments of the present invention. The collection set 200 includes a venous access device 206 (e.g., a phlebotomy needle) for withdrawing blood from a donor's arm 208, a container of anti-coagulant 210, a temporary red blood cell (RBC) storage bag 212 (which is optional depending on the blood component being collected and the number of cycles being performed), a centrifugation bowl 214 (e.g., a blood component separation device), a saline container 217, and a final plasma collection bag 216. The blood/inlet 218 couples the venous access device 206 to an inlet port 220 of the bowl 214, the plasma/outlet line 222 couples an outlet port 224 of the bowl 214 to the plasma collection bag 216, and a saline line 223 connects the outlet port 224 of the bowl 214 to the saline container 217. An anticoagulant line 225 connects the anti-coagulant container 210 to the inlet line 218.

In addition to the components mentioned above and as shown in FIG. 3, the blood processing system 100 includes a controller 226, a motor 228, and a centrifuge chuck 230. The controller 226 is operably coupled to the two pumps 232 and 234, and to the motor 228, which, in turn, drives the chuck 230. The controller 226 is also operably coupled to and in communication with the user interface 190, and may send alarm messages, notifications, and processing/operation information to the interface 190 for display.

Figure 4:
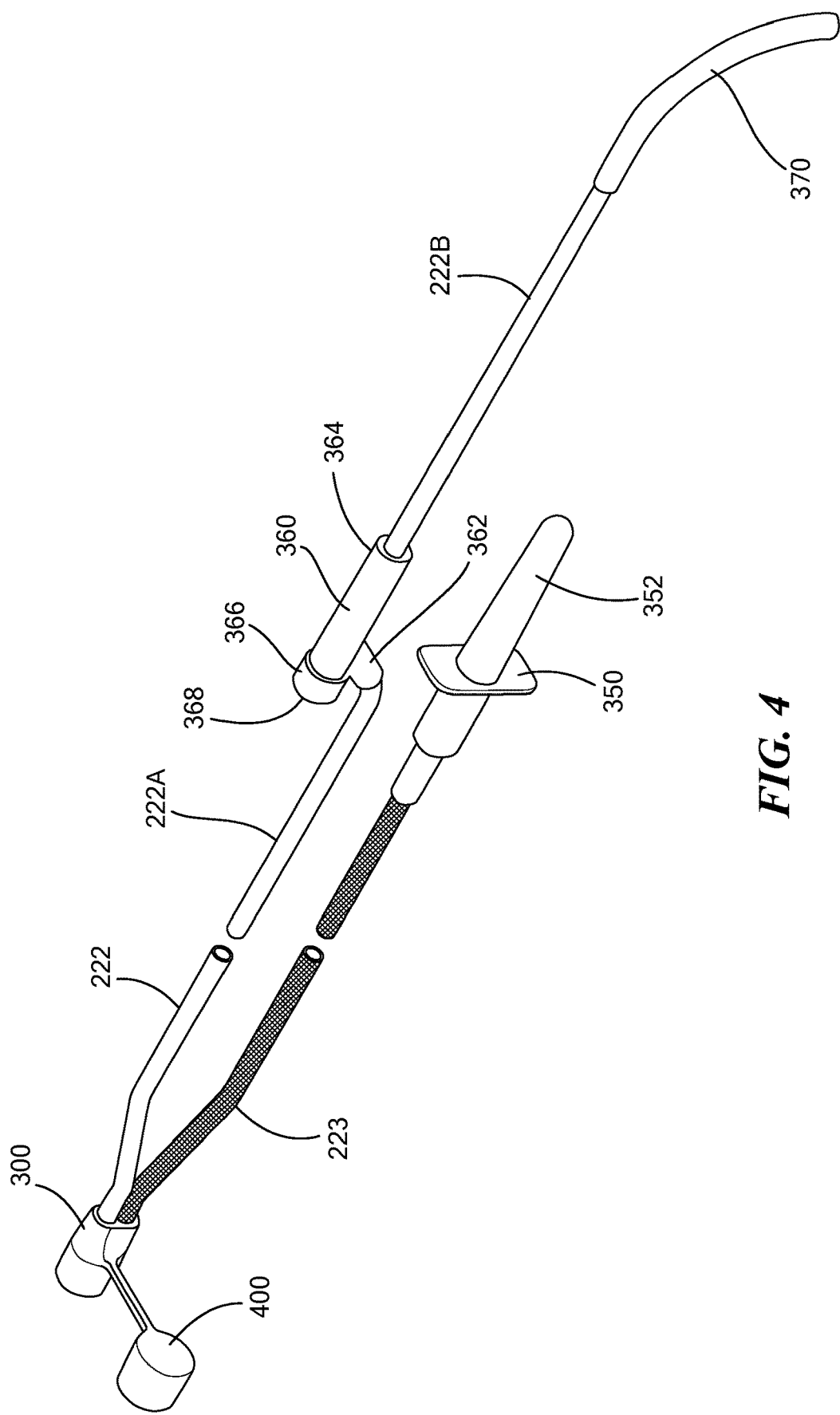
FIG. 4 schematically shows an outlet portion of the disposable set shown in FIG. 3, in accordance with some embodiments of the present invention.
Figure 5B:
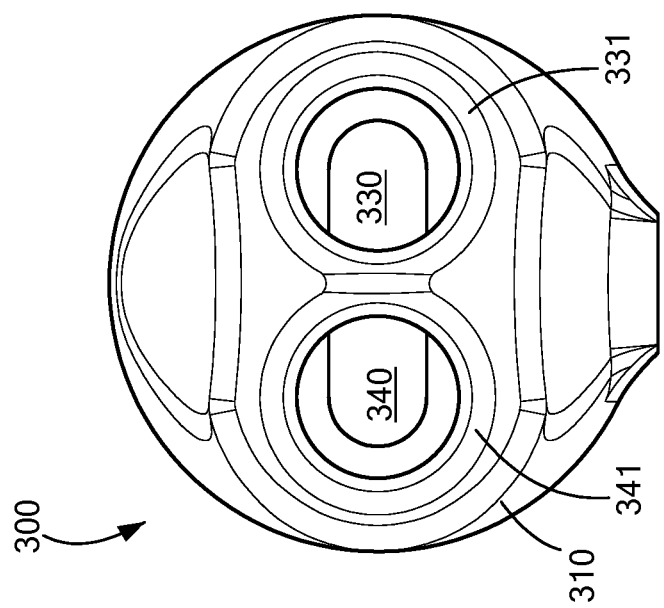
FIGS. 5A-5E schematically show various views of a bowl y-connector of the disposable set shown in FIG. 4, in accordance with some embodiments of the present invention.
Figure 5A:
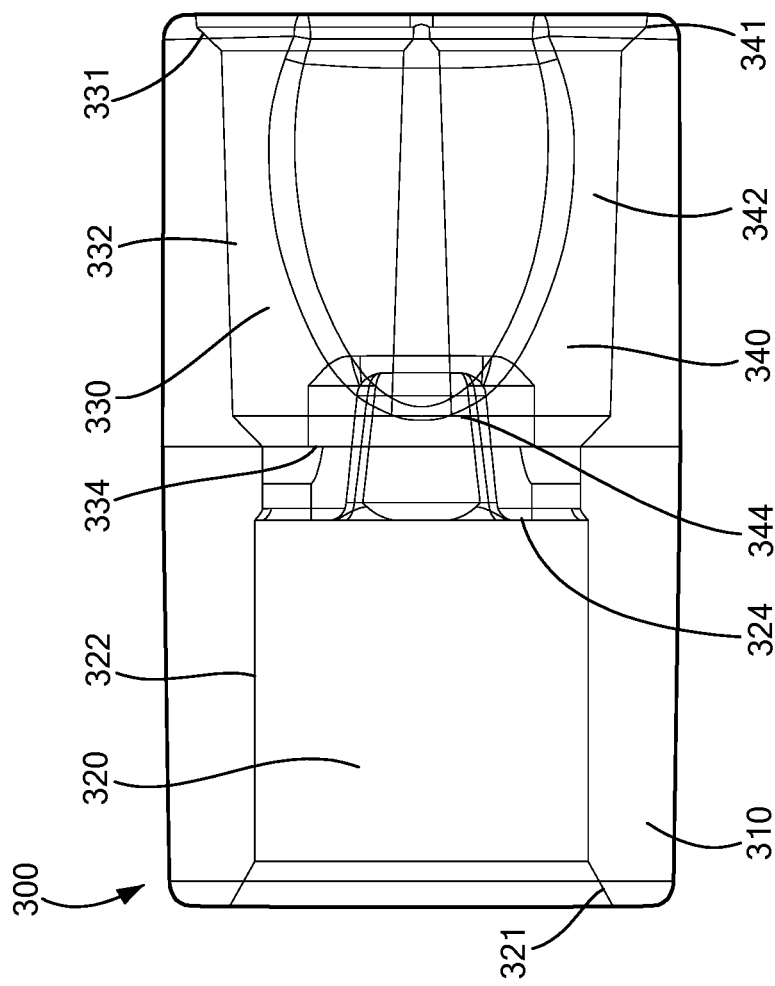
Figure 5D:
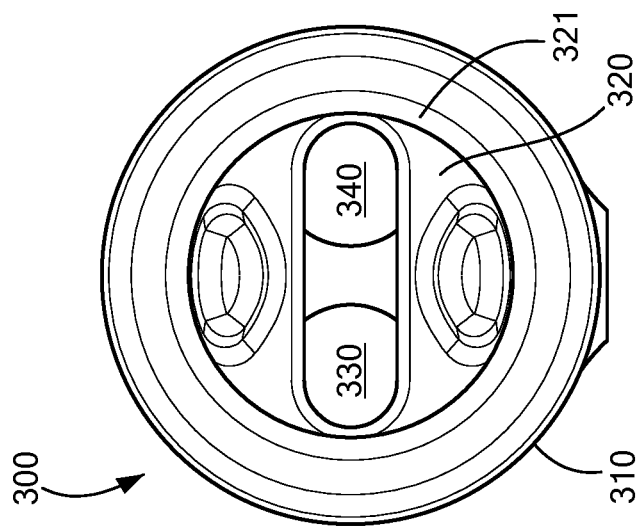
Figure 5C:
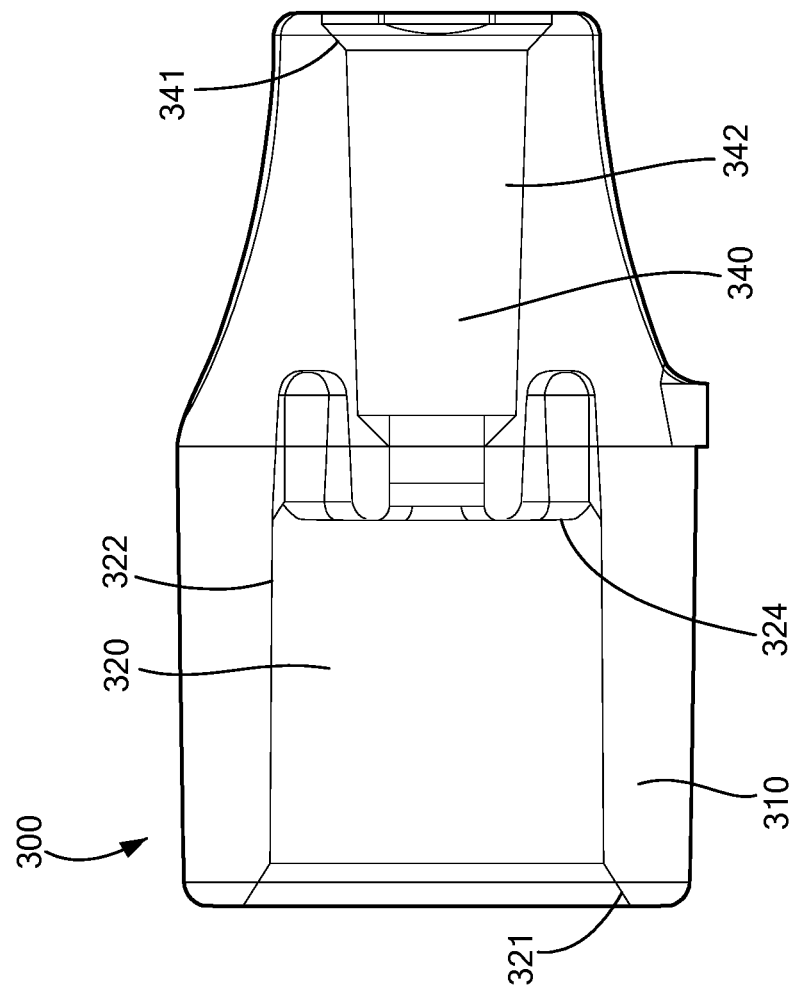
Figure 5E:
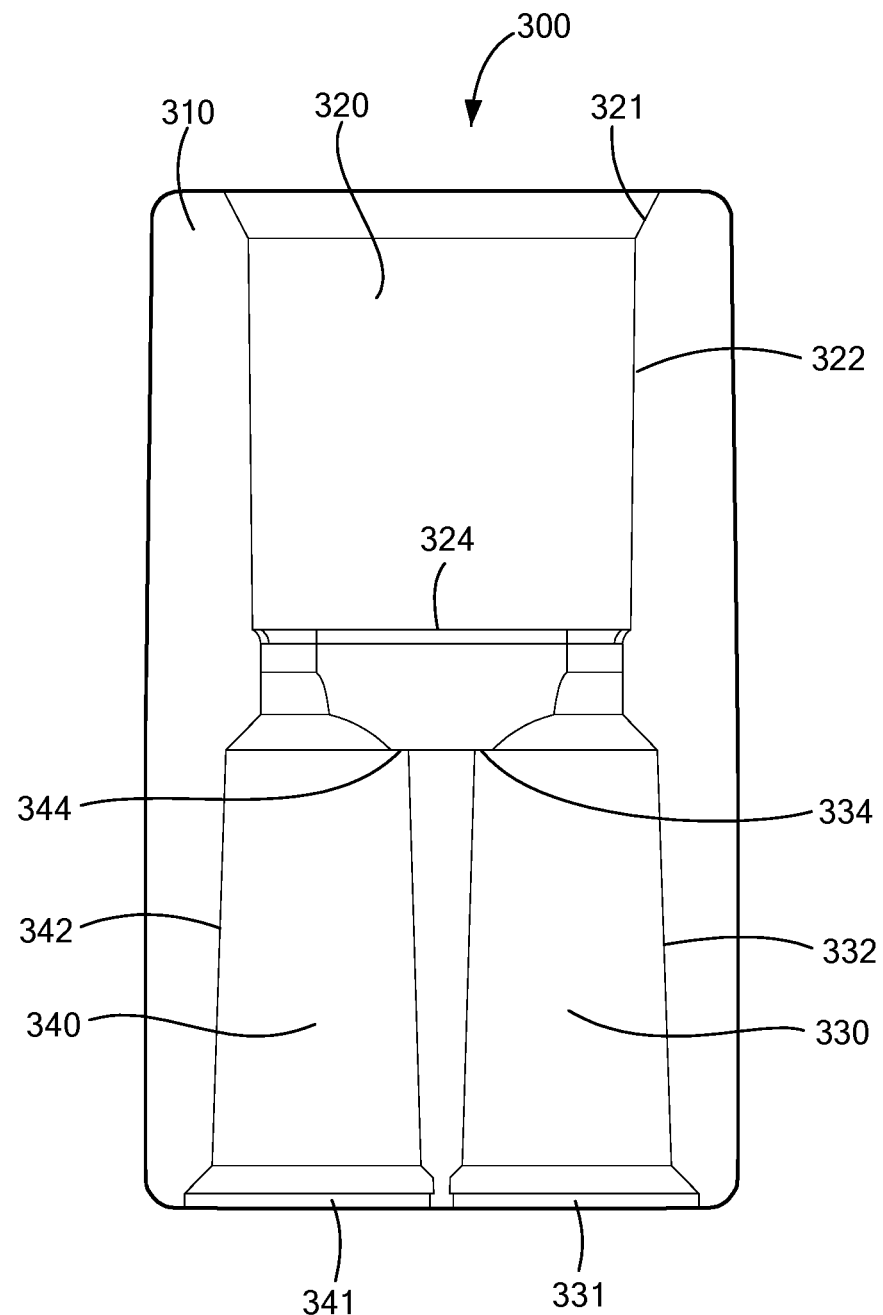
Figure 6A:
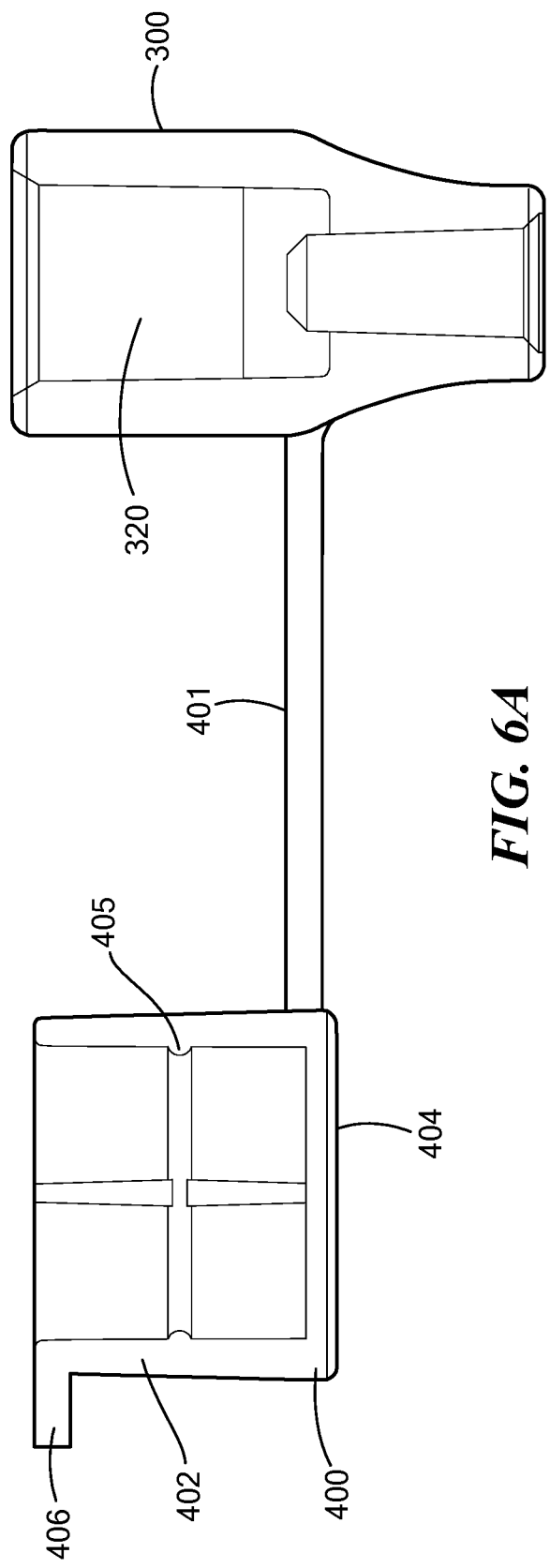
FIGS. 6A-6D schematically show a cap for the bowl y-connector shown in FIGS. 5A-5E, in accordance with additional embodiments of the present invention.
Figure 6B:
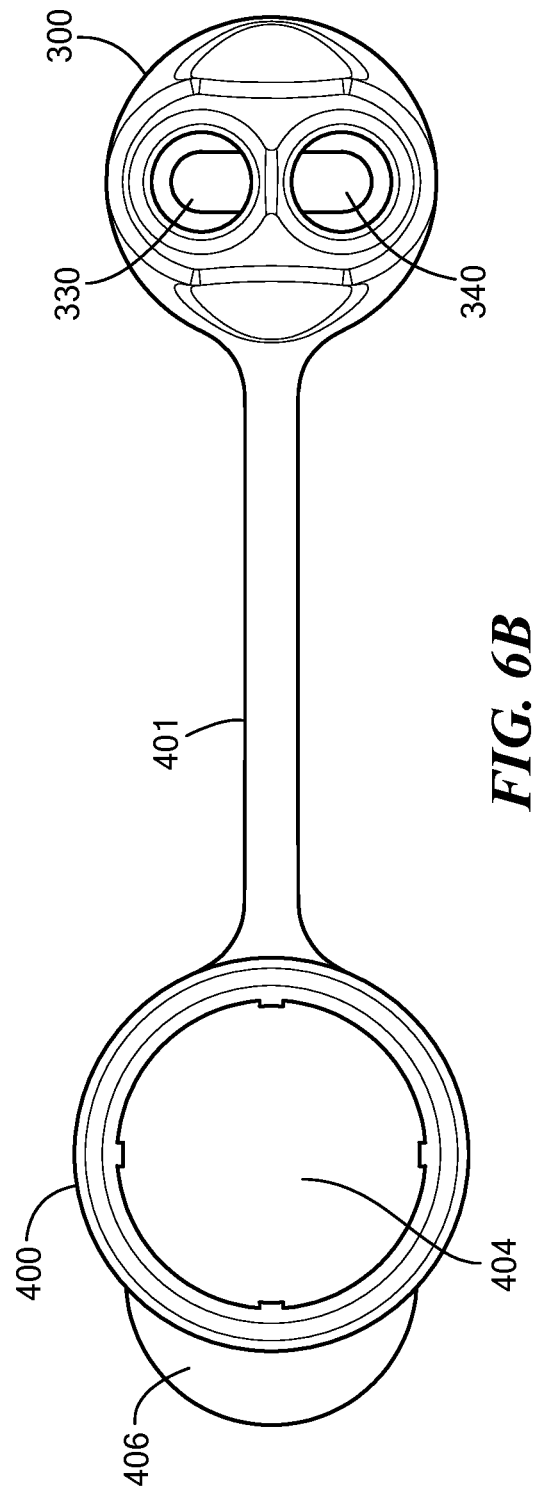
Figure 6C:
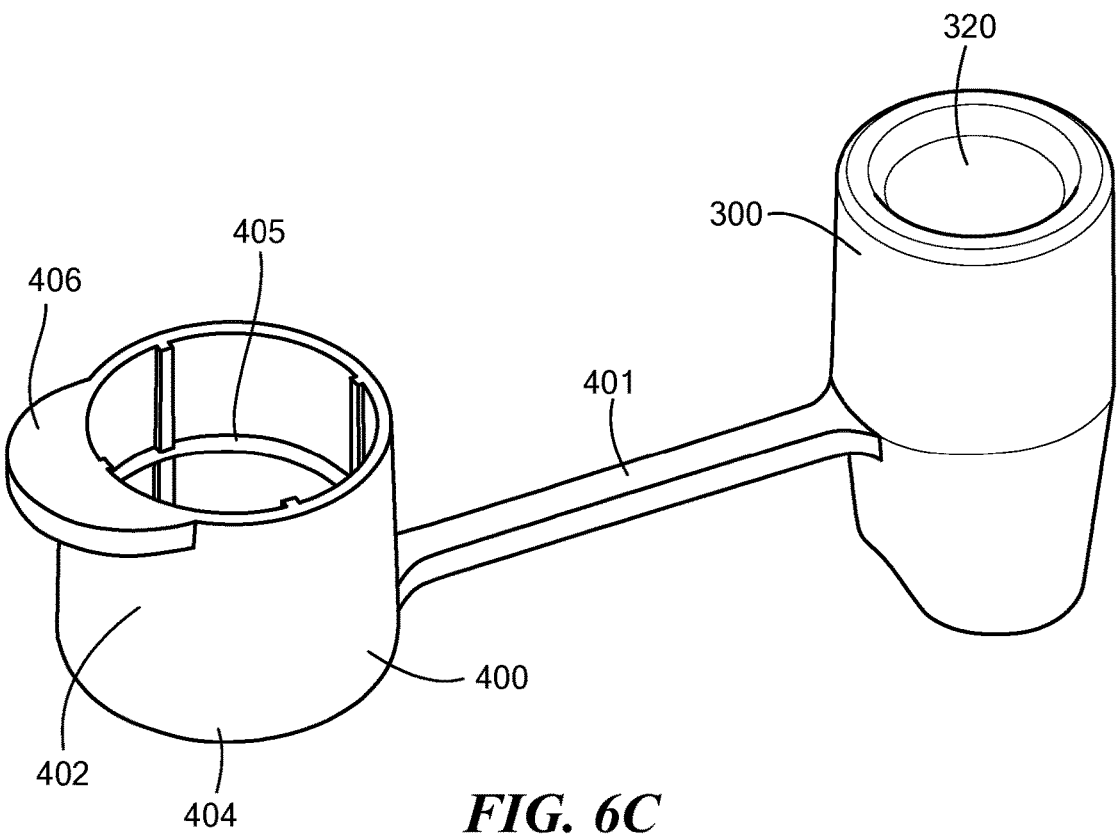
Figure 6D:
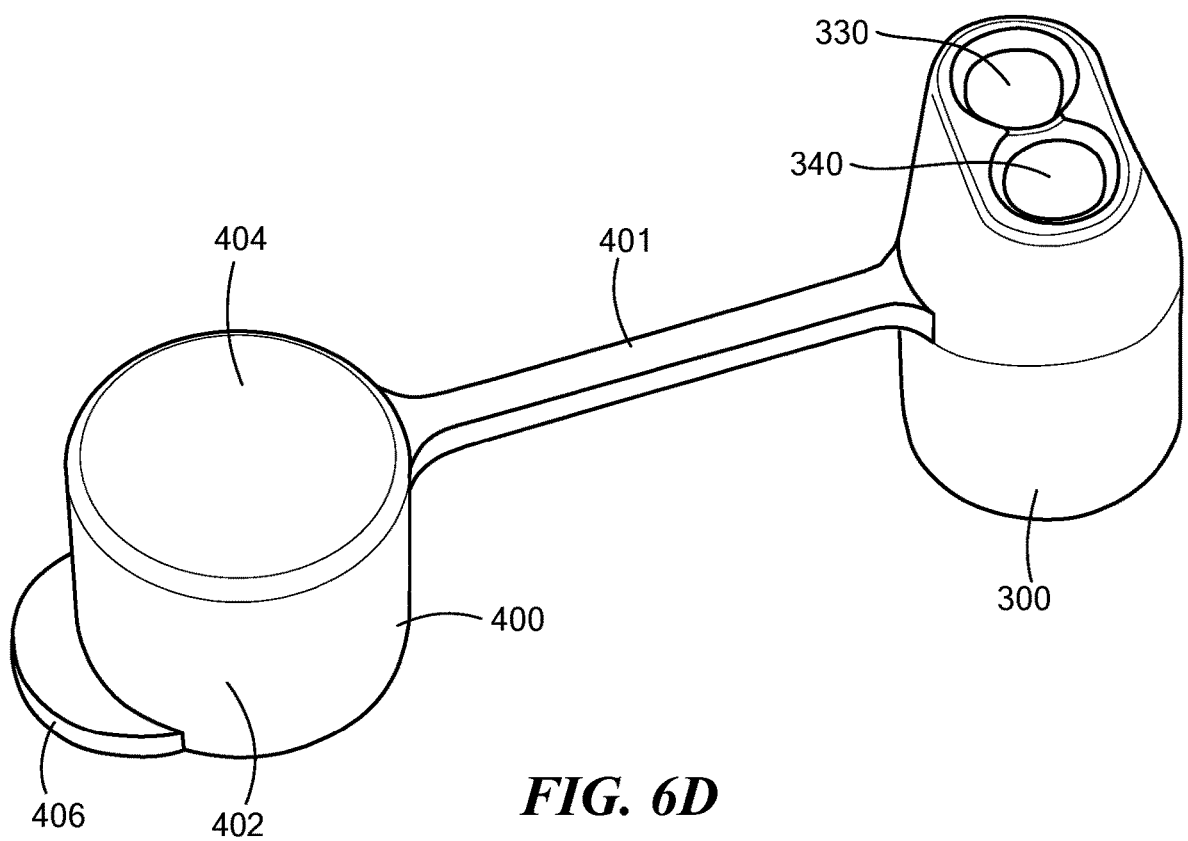

During system set-up, it is important that each of the lines remains unobstructed (unless intentionally closed by a valve) and free from kinks, twists and/or excessive/sharp bends that may restrict the flow through the lines. To that end, the outlet disposable set 200B may be designed/configured such that set 200B may be installed without kinking/twisting/excessive bending of the saline line 223 and the plasma/outlet line 222. For example, as shown in FIG. 4, the outlet disposable set 200B may include a connector 300 that connects to the bowl 214 and fluidly connects both the saline line 223 and the plasma/outline line 222 to the outlet port 224 of the bowl 214. The connector 300 may have a body 310 (FIG. 5A-5E) that defines the structure of the connector 300. At one end of the body 310 (e.g., the end that connects to the howl 214), the connector 300 can include a recess 320 (e.g., an inlet port 3211 that allows the connector 300 to be connected to the outlet port 224 of the bowl 214 (e.g., the connector 300 may be placed over the outlet port 224 such that the outlet port 224 extends into the recess 320 and seals against the side wall 322 and end wall 324 of the recess 320).

Additionally, to allow the saline and blood components exiting the bowl 214 (e.g., plasma) to flow through the connector 300, the connector 300 may include first and second flow channels/fluid paths 330/340 (FIG. 5A-5E) that extend through the body 300 (e.g., at least between one end of the connector 300 and the recess 320) and fluidly connect the saline line 223 and the plasma/outlet line 222 with the outlet port 224 of the bowl 214 (e.g., via the recess 320). For example, the end of the plasma/outlet line 222 may be inserted into a larger diameter portion 332 (e.g., at an outlet port 331) of the first flow channel 330 (e.g., up to step 334) and secured within the first flow channel 330 (e.g., glued, ultrasonically welded, solvent bonded, etc.). Similarly, the end of the saline line 223 may be inserted into a larger diameter portion 342 of the second flow channel 340 (e.g., at a saline/second inlet port 341) and secured within the second flow channel 340 (e.g., glued, ultrasonically welded, solvent bonded, etc.). To ease the connection to the bowl 214 and insertion of the plasma/outlet line 222 and saline line 223 into the flow channels 330/340, the openings of the recess 320 and flow channels 330/340 may be angled/chamfered.

Returning to FIG. 4, the saline line 223 may include a connector 350 located at one end of the saline line (e.g., the end opposite the end that is secured to the bowl connector 300). As discussed in greater detail below, the connector 350 may be a spike that is inserted into the saline container 217 to allow saline to flow through the saline line 223 and into the bowl 214 via the bowl connector 300 and outlet port 224. To maintain the cleanliness of the connector 350 (e.g., the spike) and to protect the user from accidentally injuring themselves on the spike, the connector 350 may include a cover 352 that may be removed just prior to connecting the connector 350 to the saline container 217.

As best shown in FIG. 4, the plasma/outlet line 222 may include a first portion 222A and a second portion 222B that are connected to one another via a sample site 360. For example, the sample site 360 may be y-site with three ports. The first portion 222A may be connected to one of the ports (e.g., y-site port 362) and extend between the y-site port 362 and the bowl connector 300. The second portion 222B may be connected to a second port 364 of the sample site 360 and extend between the second port 364 and the plasma collection container 216 (e.g., when the outlet set 200B is connected/installed). As discussed in greater detail below, once the plasma has been collected within the container 216, there may be a need to sample the collected plasma at various times (e.g., after collection, sometime during storage, prior to use). To that end, the third port 366 of the sample site 360 may include a septum 368. During sampling, the user may draw plasma from the container 216 and into the outlet/plasma line (e.g., by using a pump, turning the container 216 upside down, and/or by gently squeezing the walls of the container 216 to force plasma into the line 222) and insert a sample collection container holder (e.g., a vacutainer holder) into the septum 368 to access/sample plasma within the outlet/plasma line 222. The user may then connect a vacutainer to the holder to begin collecting a sample of plasma within the vacutainer.

As mentioned above kinking, twisting, and/or severe bending of the fluid lines (e.g., the saline line 223 and plasma/outlet line 222) can be problematic and negatively impact the performance of the blood processing system. To help reduce the risk of kinking and severe bending, some embodiments of the outlet disposable set 200B may have other features that ease installation of the disposable sets 200A/200B and help maintain proper flow through the plasma/outlet line 222. For example, as shown in FIG. 4, a section of the second portion 222B of the plasma/outline line 222 (e.g., near the end that connects to the plasma container 216) may be preformed with a curve (e.g., a section of the plasma/outlet line 222 may have a portion that remains curved even when not exposed to external stresses/forces—it is curved when in the at rest state). This curved portion 370 reduces the stress on the connection between the plasma/outlet line 222 and the plasma storage container 216 and reduces the risk of kinking/twisting.

It is important to note the curved portion 370 may be formed directly into the second portion 222B of the plasma/outline line 222 (e.g., the second portion 222B and the curved portion 370 may be a single piece). Alternatively, the curved portion 370 may be a separate piece that is preformed with the curve and secured to the second portion 222B. For example, the curved portion may be solvent bonded to the second portion 222B.

As noted above, it is important to maintain the cleanliness and sterility of the system and disposable sets 200A and 220B prior to connection to the system 100 and bowl 214. To that end and as shown in FIGS. 6A-6D, some embodiments of the outlet disposable set 200B may include a cap 400 that may be used to cover the bowl connector 300 (e.g., the recess 320/end that connects to the bowl 214) when the disposable set 200B is not connected to the bowl 214. For example, the cap 400 may include a skirt 402 that extends from the body 404 of the cap 400. Additionally, the cap may also include a rib 405 that extends inward from the inner surface of the skirt 402. To connect the cap 400 to the connector 300, the skirt 402 may be placed over the inlet 321 of the connector 300. As the cap 400 is connected and the skirt 402 is placed over the inlet 321 of the connector 300, the rib 405 interfaces with the surface of the bowl connector 300 to create a liquid-tight seal and prevent egress of fluid from the connector 300, for example, following collection (e.g., plasma collection) and replacement of the cap 400.

As discussed in greater detail below, the user/technician may remove the cap 400 just prior to connection to the bowl 214. However, at this time, the user/technician will likely be wearing gloves which can make it difficult to grasp and hold the cap 400, particularly, if the user/technician has any liquid/moisture on their gloves (e.g., water, isopropyl alcohol, etc.). To help the user remove the cap 400 from the bowl connector 300, the cap may include a pull-tab 406 that the user/technician may grasp during removal. Additionally, to help prevent the user from losing and/or accidentally dropping the cap 400 after removal, the cap 400 may be secured to the bowl connector 300 via a tether 401.

In addition to the structural differences between the plasma/outlet line 222 and the saline line 223 (e.g., the connector 350, the curved portion 370, the sample site 360, etc.), some embodiments of the outlet disposable set 200B may include additional features to help distinguish between the plasma/outlet line 222 and saline line 223 and help prevent the user from improperly installing the outlet disposable set 200B. For example, one or more of the lines 222/223 may include an indicator that marks which line is which. For example, the saline line 223 may be marked with the word "saline" along the length of the saline line 223, and/or the plasma/outline line 222 may be marked with the word "plasma" or dots/lines along the length of the line 222. The indicators may be printed on the lines 222/223 or hot-stamped on the lines 222/223. Additionally or alternatively, the saline line 223 may be tinted a different color (e.g., blue) as compared to the plasma/outlet line 222 (e.g., the lines 222/223 may be color coded).

Figure 7:
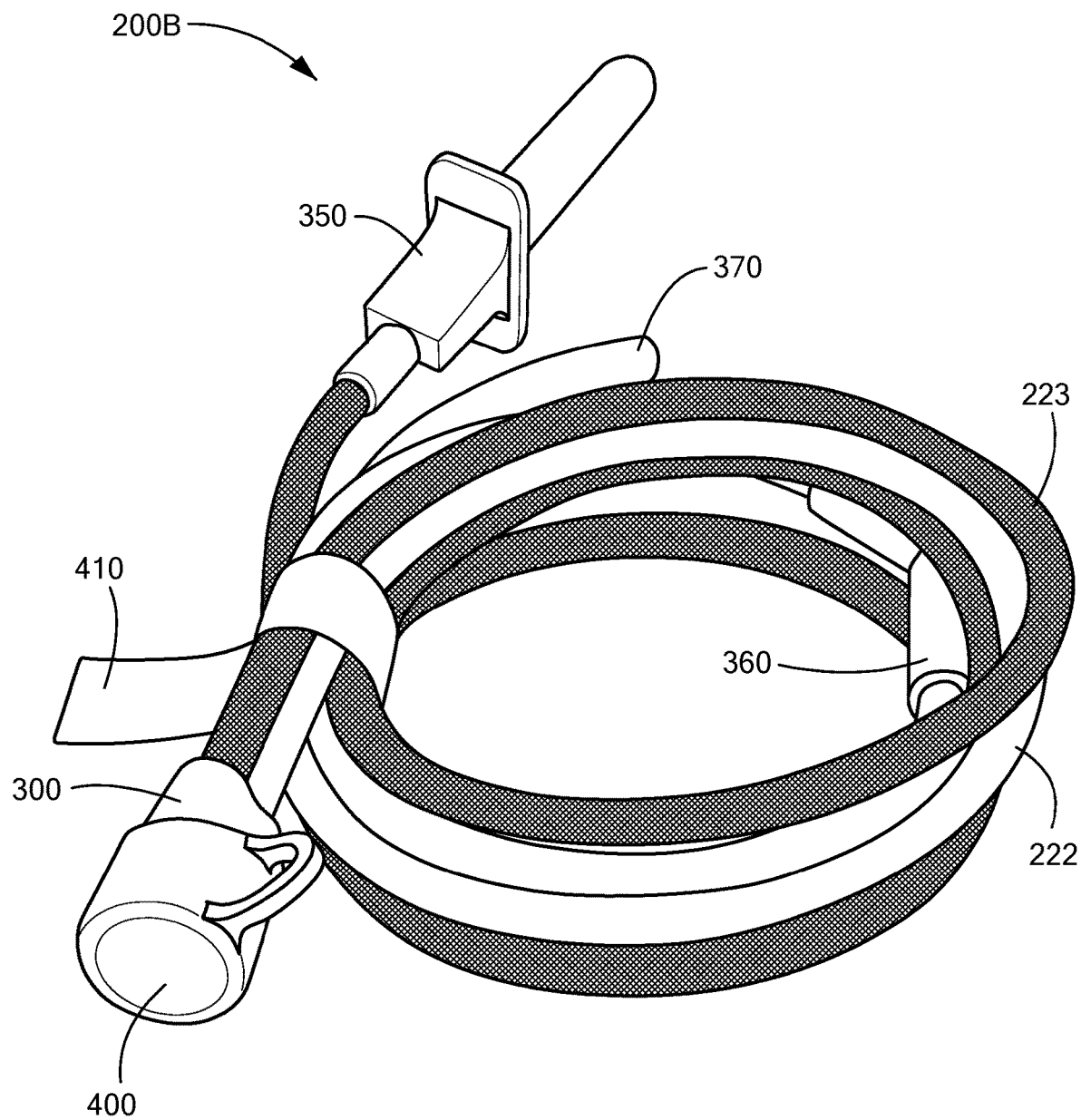
FIG. 7 schematically shows the disposable set of FIG. 4 coiled-up for packaging/storage, in accordance with some embodiments of the present invention.
Figure 8:
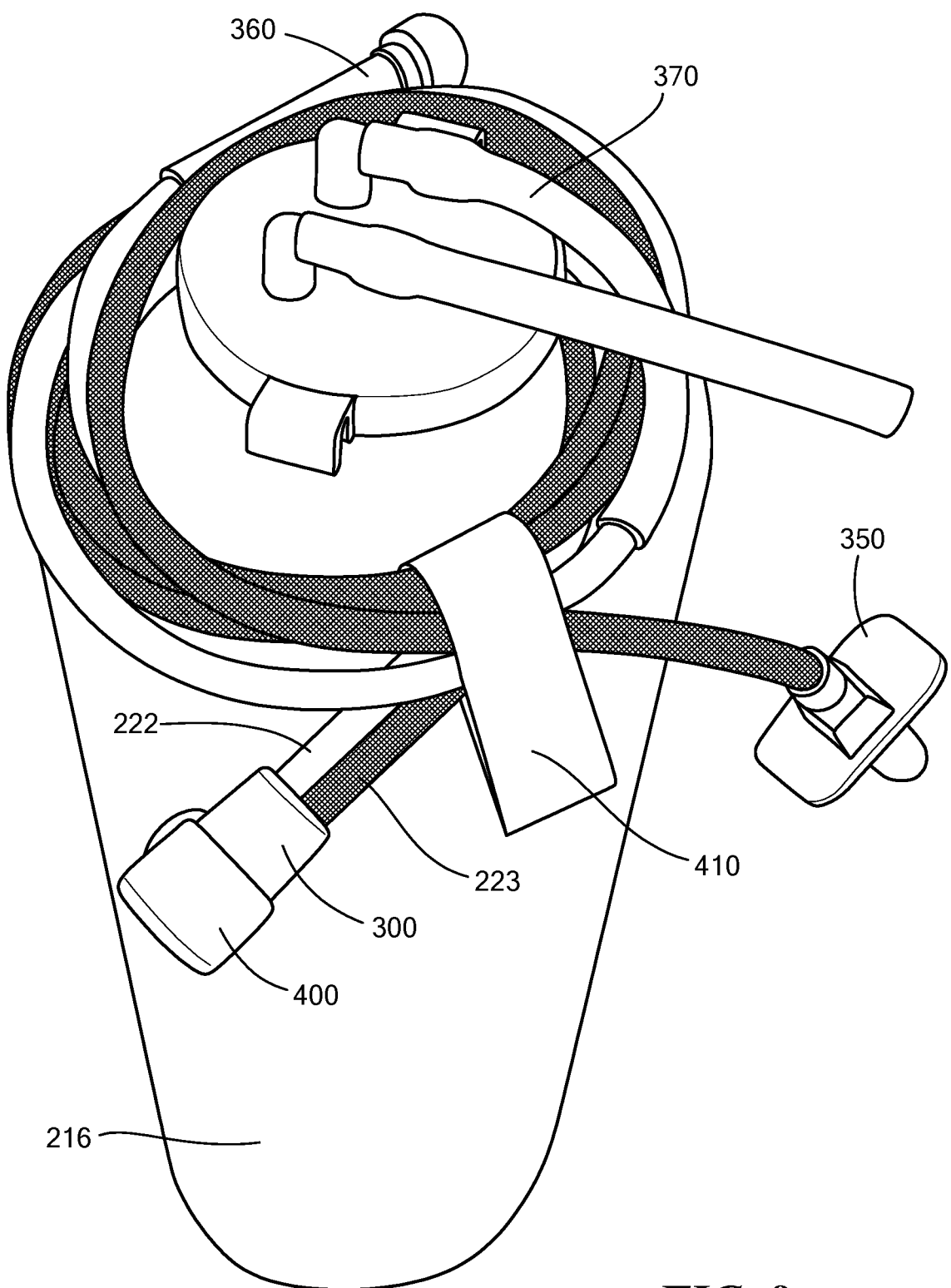
FIG. 8 schematically shows the disposable set of FIG. 4 coiled-up for packaging/storage and attached to a plasma bottle, in accordance with further embodiments of the present invention.

As shown in FIG. 7, during storage, the outlet disposable set 200B may be coiled up and held together with a piece of tape 410, string, a tie-wrap, or similar securement structure. Additionally or alternatively, in embodiments in which the outlet disposable set 200B (e.g., the plasma/outlet line 222) is pre-secured/connected to the plasma container 216 (FIG. 8), the outlet disposable set 200B may be wrapped around the neck of the container 216. In either case, the curved portion 370 of the outlet disposable set 200B helps the outlet disposable set 200B to be easily coiled without kinking, twisting, etc.

In operation, the disposable collection set 200 (e.g., the inlet disposable set 200A and the outlet disposable set 200B) may be loaded onto/into the blood processing system 100 prior to blood processing. In particular, the blood/inlet line 218 is routed through the blood/first pump 232 and the anticoagulant line 225 from the anti-coagulant container 210 is routed through the anticoagulant/second pump 234. The centrifugation bowl 214 may then be securely loaded into the chuck 230. As noted above, to help the user/technician connect the tubing (e.g., to reduce setup errors when interfacing the disposable set with the line sensor 185), tubing 222 (e.g., the plasma collection line) and/or tubing 223 (e.g., the saline line) may be color-coded, marked with text or symbols, or otherwise distinct from the other tubing. For example, tubing 223 may be colored blue and/or marked with the text "saline" to indicate that it is the saline line. Similarly, tubing 222 may be clear (or a color other than blue) and/or marked with the text "plasma" to indicate that it is the plasma line.

Figure 9A:
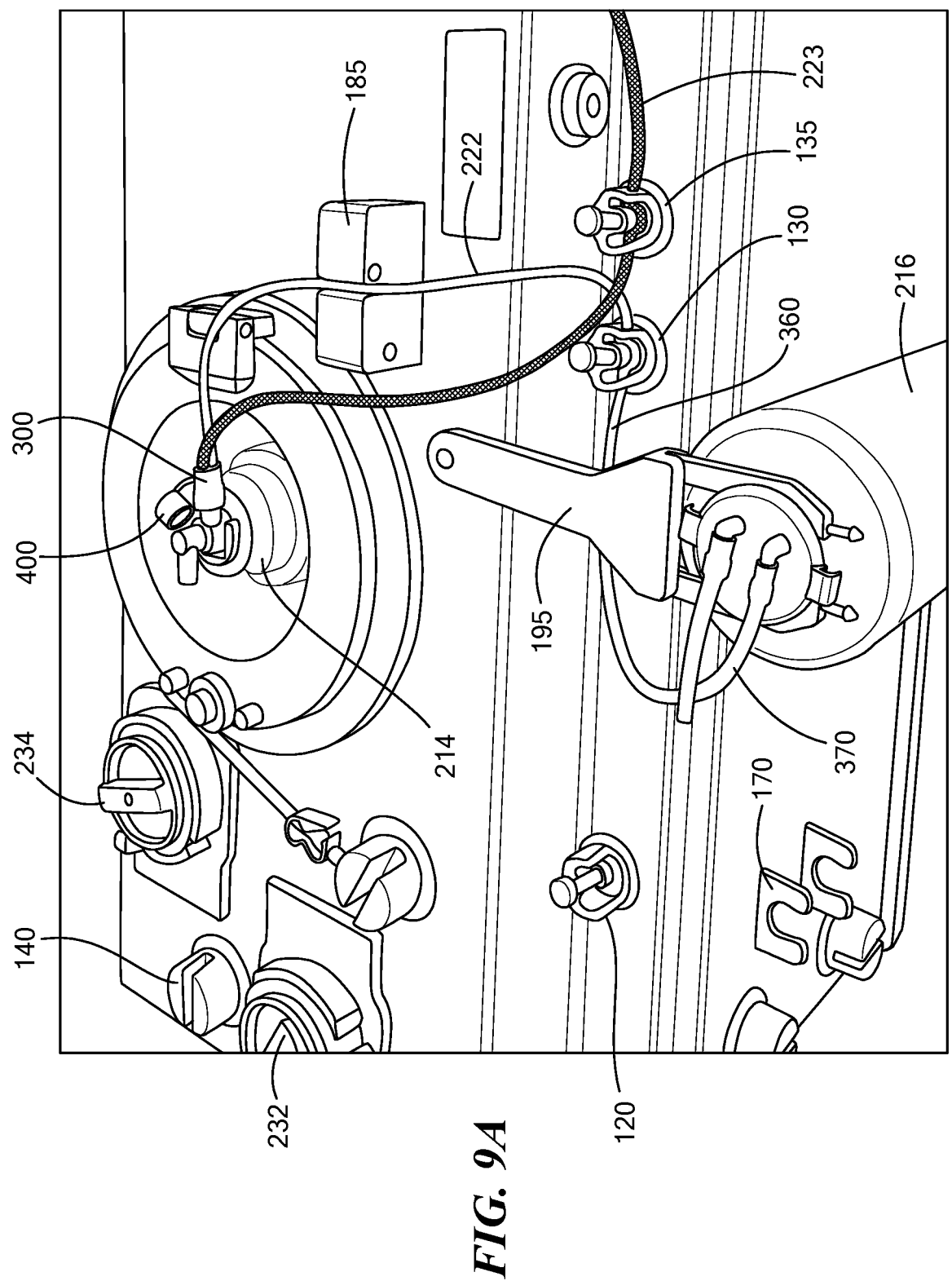
FIGS. 9A-9C show the disposable set of FIG. 4 installed in the blood processing system, in accordance with some embodiments of the present invention.
Figure 9B:
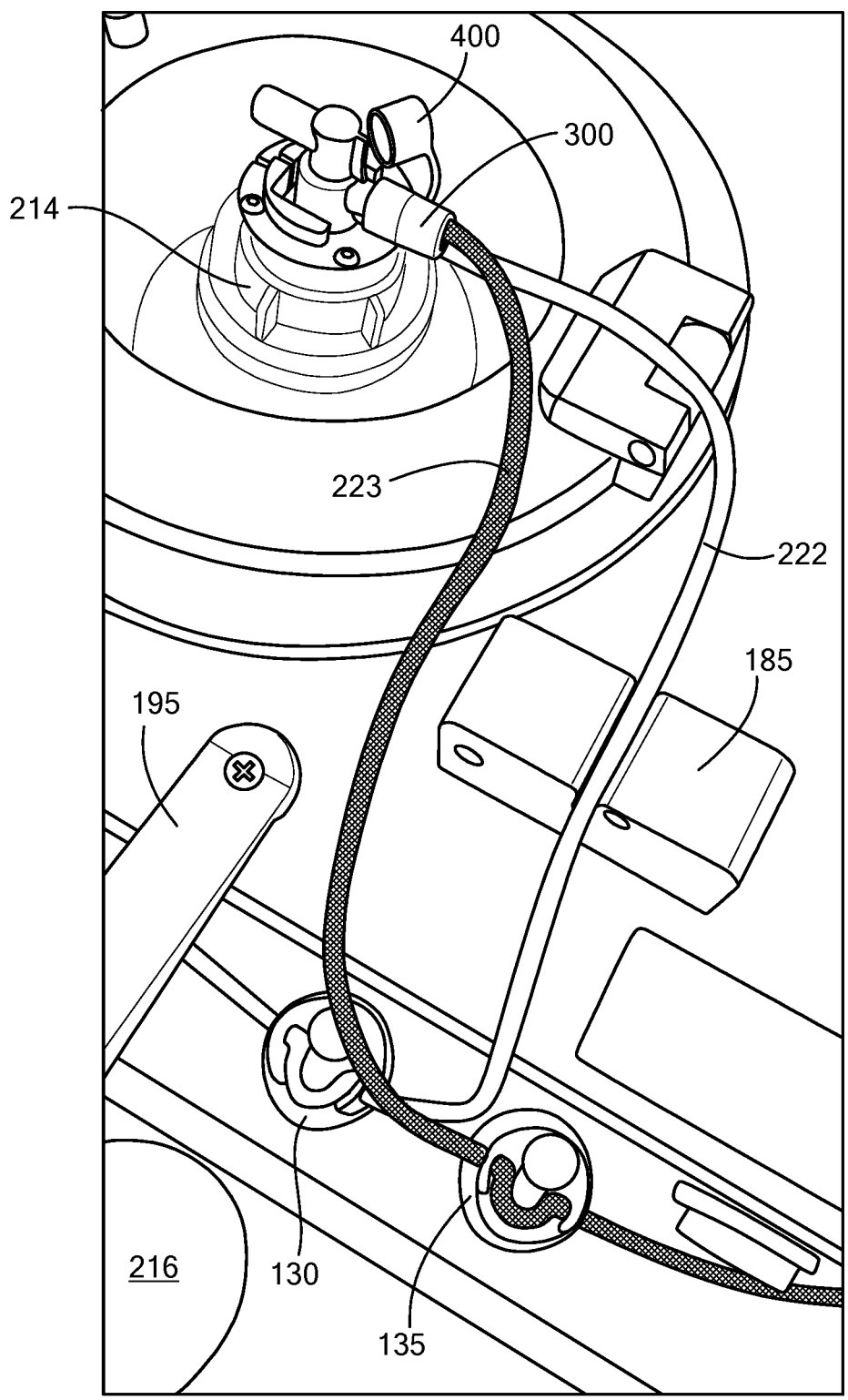
Figure 9C:
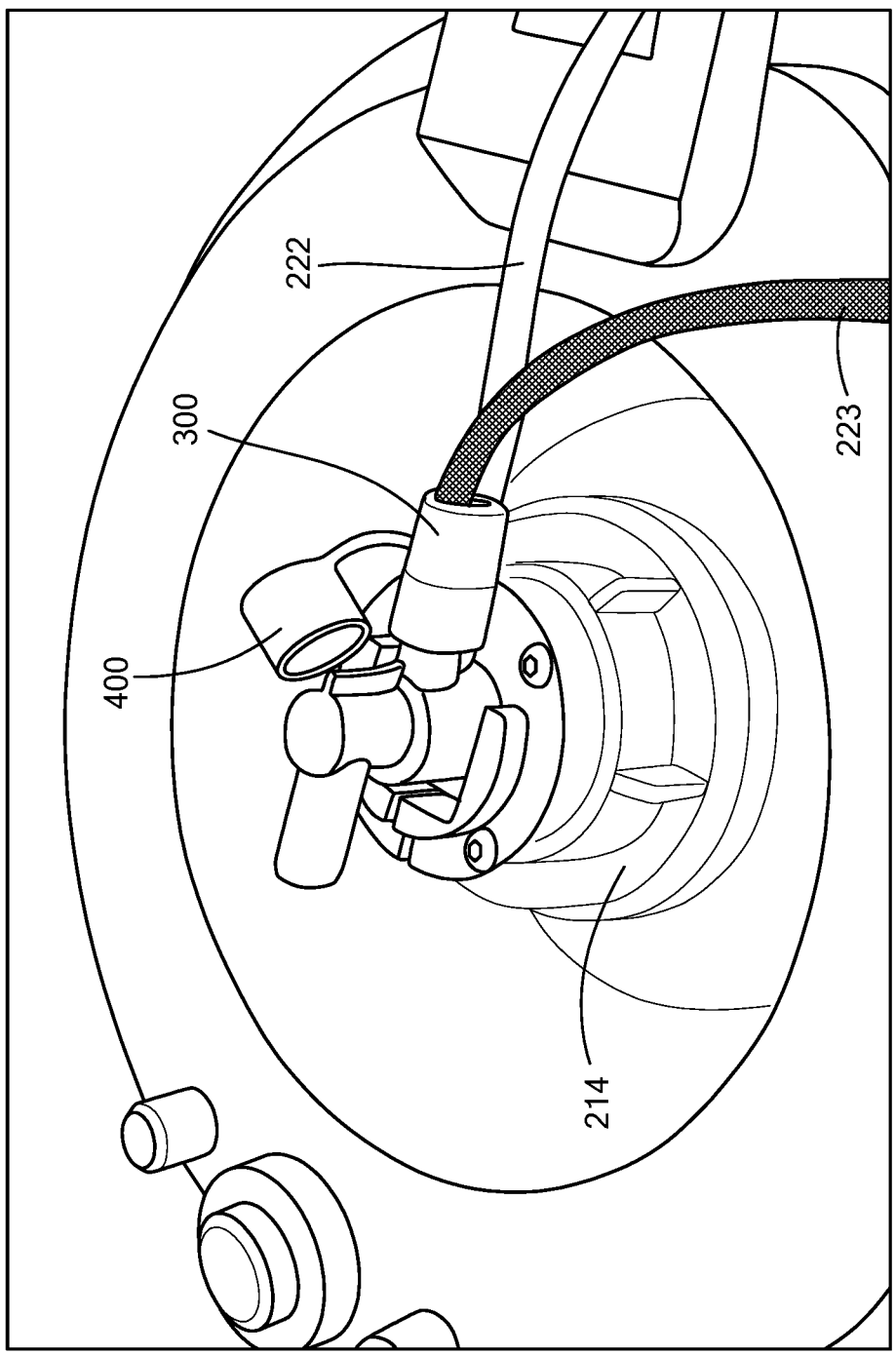

To install the outlet disposable set 200B, the user may remove the cap 400 from the bowl connector 300 and connect the connector 300 to the outlet 224 of the bowl 214 (FIGS. 9A-9C). The user may then run/connect the plasma/outline line 222 and saline line 223 to their respective components and install the plasma container 216 into the weight sensor 195 (FIG. 9A). For example, the user may run the saline line 223 through valve 135, run the plasma/outlet line 222 through valve 130 and the line sensor 185 (FIGS. 9A and 9B), and insert the connector/spike 350 into the saline container 217. Once the lines 222/223 are in place, the user may insert the venous access device 206 into the donor's arm 208. Next, the controller 226 activates the two pumps 232, 234 and the motor 228. Operation of the two pumps 232, 234 causes whole blood from the donor to be mixed with anti-coagulant from container 210 and delivered to the inlet port 220 of the bowl 214.

The anticoagulant line 225 may also include a bacteria filter (not shown) that prevents any bacteria in the anticoagulant source 210, the anticoagulant, or the anticoagulant line 225 from entering the system 100 and/or the subject. Additionally, the system 100 may include an air detector 140 that detects the presence of air within the anticoagulant. The presence of air bubbles within any of the system lines can be problematic for the operation the system 100 and may also be harmful to the subject if the air bubbles enter the blood stream. Therefore, the air detector 140 may be connected to an interlock that stops the flow within the anticoagulant line 225 in the event that an air bubble is detected (e.g., by stopping the anticoagulant pump 234 or closing a valve on the anticoagulant line 225), thereby preventing the air bubbles from entering the subject.

Once a desired amount of anti-coagulated whole blood is withdrawn from the subject and contained within the blood component separation device 214, the blood component separation device 214 separates the whole blood into several blood components. For example, the blood component separation device 214 may separate the whole blood into a first, second, third, and, perhaps, fourth blood component. More specifically, the blood component separation device 214 (and the centrifugal forces created by rotation of the separation device 214) can separate the whole blood into plasma, platelets, red blood cells, and, perhaps, white blood cells. The higher density component, i.e., RBC, is forced to the outer wall of the bowl 214 while the lower density plasma lies nearer the core. A buffy coat is formed between the plasma and the RBC. The buffy coat is made up of an inner layer of platelets, a transitional layer of platelets and WBC and an outer layer of WBC. The plasma is the component closest to the outlet port and is the first fluid component displaced from the bowl 214 via the outlet port 224 as additional anticoagulated whole blood enters the bowl 214 through the inlet port 220.

The system 10 may also include an optical sensor (not shown) that may be applied to a shoulder portion of the bowl 214. The optical sensor monitors each layer of the blood components as they gradually and coaxially advance toward the core from the outer wall of the bowl 214. The optical sensor may be mounted in a position (e.g., within the well 180) at which it can detect the buffy coat reaching a particular radius, and the steps of drawing the whole blood from the subject/donor and introducing the whole blood into the bowl 12 may be altered and/or terminated in response to the detection.

Once the blood component separation device 214 has separated the blood into the various components, one or more of the components can be removed from the blood component separation device 214. For instance, the plasma may be removed to the plasma container 216 (e.g., a plasma bottle) through line 222. As noted above, some embodiments of the system 100 may include a weight sensor 195 (FIGS. 1 and 9A) that measures the amount plasma collected. The plasma collection process may continue until the desired volume of plasma is collected within the plasma collection container 216. Although not shown, if the blood processing system 100 and disposable set 200 include platelet, red blood cell, and/or white blood cell bags, each of the bags/containers may include similar weight sensors (e.g., load cells).

In some embodiments, the system 100 may also include a line sensor 185 (mentioned above) that can determine the type of fluid (e.g., plasma, platelets, red blood cells etc.) exiting the blood component separation device 214. In particular, the line sensor 185 consists of an LED which emits light through the blood components leaving the bowl 214 and a photo detector which receives the light after it passes through the components. The amount of light received by the photo detector is correlated to the density of the fluid passing through the line. For example, if plasma is exiting the bowl 214, the line sensor 185 will be able to detect when the plasma exiting the bowl 214 becomes cloudy with platelets (e.g., the fluid existing the bowl 214 is changing from plasma to platelets). The system 100 may then use this information to either stop the removal of blood components from the bowl 214, stop drawing whole blood from the subject, or redirect the flow by, for example, closing one valve an opening another.

Once the system 100 removes the desired components (e.g., plasma) from the blood component separation device 214, the system 100 can return the remaining components to the subject. For example, when all the plasma has been removed and the bowl 214 is full of RBCS (and any other blood component not collected), the controller 226 stops the draw of whole blood from the subject and reverses the direction of the blood/first pump 232 to draw the RBCs and other components) from the bowl 214 to a temporary RBC collection bag 212 or directly back to the subject. Alternatively, if the system 100 is so equipped, the system may return the components to the subject via a dedicated return line.

In addition to the non-collected blood components (e.g., the components remaining in the bowl 214), the system 100 may also return saline to the patient/subject. The saline may be used as a compensation fluid to make up for the volume of the blood component (e.g., plasma) that was removed and collected, and is not being returned to the patient. To that end, during the return step (e.g., the step of returning the remaining blood components to the patient), the saline valve 135 may be opened to allow saline from the saline container 217 to flow through the saline line 223 and into the bowl 214 (via connector 300), where it can be returned to the patient/donor with or after the remaining blood components. Once the bowl 214 is emptied and if additional plasma is to be collected, the collection and separation of whole blood from the donor may be resumed.

It should be noted that by incorporating the features discussed above (e.g., the connector 300 and curved portion 370), various embodiments can minimize and/or prevent the lines 222/223 from twisting/kinking/bending sharply. Additionally, by color coding and/or marking the lines 222/223, embodiments of the present invention are also able to minimize user error during installation and set-up. Therefore, various embodiments of the present invention are able to improve system performance, reduce user error and ease installation/set-up.

It is also important to note that, although the various embodiments discussed above are in relation to a blood processing system that collects plasma, the features discussed herein may be applied to any type of blood processing system. For example, the features described herein may be implemented on blood processing systems that collect and/or process red blood cells, platelets and/or white blood cells.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A tubing set for a blood processing system comprising:
a first connector configured to connect directly to a centrifuge bowl within the blood processing system, the first connector having a body with a first end and a second end, the first connector also having a first inlet located within first end and configured to be fluidly connected to an outlet of the centrifuge bowl, the first connector also having an outlet located within the second end and a second inlet located within the second end;
a first tube fluidly connected to the outlet and configured to fluidly connect the centrifuge bowl and a final blood component storage container, the final blood component storage container configured to collect a blood component to be collected; and
a second tube fluidly connected to the second inlet and configured to fluidly connect the centrifuge bowl and a saline storage container, the second tube including a second connector configured to connect to the saline storage container.

2. A tubing set according to claim 1, wherein the second connector is a spike.

3. A tubing set according to claim 1, wherein the tubing set includes a cap, the cap configured to cover the first inlet of the first connector when the first connector is not connected to the centrifuge bowl.

4. A tubing set according to claim 3, wherein the cap is tethered to the first connector.

5. A tubing set according to claim 3, wherein the cap makes a liquid-tight seal on the first connector.

6. A tubing set according to claim 3, wherein the cap includes a rib extending from an inner surface of the cap, the rib configured to seal against an outer surface of the first connector.

7. A tube set according to claim 3, wherein the cap includes a tab extending from a surface of a body of the cap, the tab configured to allow a user to remove the cap from the first connector when connected.

8. A tubing set according to claim 1, wherein the second tube is tinted.

9. A tubing set according to claim 1, wherein the second tube includes at least one marking to indicate that the second tube is configured to be connected to the saline storage container.

10. A tubing set according to claim 9, wherein the at least one marking includes text indicating that the second tube is configured to be connected to the saline storage container.

11. A tubing set according to claim 1, wherein the first tube includes at least one marking to indicate that the first tube is configured to be connected to the final blood component storage container.

12. A tubing set according to claim 11, wherein the at least one marking includes dots and/or lines.

13. A tubing set according to claim 1, wherein the first and second tubes are color coded.

14. A tubing set according to claim 1, wherein the first tube has a first portion and second portion.

15. A tubing set according to claim 14, wherein the second portion includes a pre-curved section, one end of the pre-curved section configured to connect to the final blood component storage container.

16. A tubing set according to claim 15, wherein the pre-curved section is integrally formed with the second portion.

17. A tubing set according to claim 15, wherein the pre-curved section is solvent bonded to the second portion.

18. A tubing set according to claim 14, wherein the first tube includes a sample site located between the first portion and the second portion.

19. A tubing set according to claim 18, wherein the sample site includes a sample site inlet fluidly connected to the first portion, a sample site outlet fluidly connected to the second portion, and a sample port.

20. A tubing set according to claim 19, wherein the sample port includes a septum, the septum configured to seal the sample port.

21. A tubing set according to claim 20, wherein the sample site is configured to receive a sample collection container holder.

22. A tubing set according to claim 1, wherein the outlet includes a first fluid path fluidly connecting the first inlet and the outlet, a diameter of the first fluid path expanding toward the outlet.

23. A tubing set according to claim 1, wherein the second inlet includes a second fluid path fluidly connecting the first inlet and the second inlet, a diameter of the second fluid path expanding toward the second inlet.

24. A tubing set according to claim 1, wherein the final blood component storage container is a plasma container.

25. A tubing set according to claim 1, wherein the first end has a first surface and the second end has a second surface, the first inlet located within the first surface, the outlet and second inlet located within the second surface.

26. A tubing set according to claim 1, further comprising:
a first fluid path extending at least partially through the connector body and fluidly connecting the first inlet and the outlet; and
a second fluid path extending at least partially through the connector body and fluidly connecting the first inlet and the second inlet, the first fluid path being parallel to the second fluid path.

27. A connector for a blood processing system comprising:
a connector body defining the structure of the connector, the connector having a first end and a second end;
a first port configured to connect directly to an outlet of a centrifuge bowl of the blood processing system, the first port located within the first end;
a second port fluidly connected to the first port and located within the second end, the second port configured to be fluidly connected to a first tube, the first tube configured to fluidly connect the second port and a final blood component storage container, the final blood component storage container configured to collect a blood component to be collected; and
a third port fluidly connected to the first port and located within the second end, the third port configured to be fluidly connected to a second tube, the second tube configured to fluidly connect the third port and a saline storage container.

28. A connector according to claim 27, further comprising;
a cap configured to cover the first port when the first port is not connected to the centrifuge bowl.

29. A connector according to claim 28, wherein the cap is tethered to the connector body.

30. A connector according to claim 28, wherein the cap makes a liquid-tight seal on the first connector.

31. A connector according to claim 28, wherein the cap includes a rib extending from an inner surface of the cap, the rib configured to seal against an outer surface of the first connector.

32. A connector according to claim 28, wherein the cap includes a tab extending from a surface of a body of the cap, the tab configured to allow a user to remove the cap from the first connector when connected.

33. A connector according to claim 27, further comprising:
a first flow channel extending at least partially through the connector body and fluidly connecting the first port and the second port; and
a second flow channel extending at least partially through the connector body and fluidly connecting the first port and the third port, a diameter of the second flow channel expands toward the third port.

34. A connector according to claim 27, wherein the final blood component storage container is a plasma container.

35. A connector according to claim 27, wherein the first end has a first surface and the second end has a second surface, the first port located within the first surface, the second and third ports located within the second surface.

36. A connector according to claim 27, further comprising:
a first flow channel extending at least partially through the connector body and fluidly connecting the first port and the second port; and
a second flow channel extending at least partially through the connector body and fluidly connecting the first port and the third port, the first flow channel being parallel to the second flow channel.

* * * * *